United States Patent
Wang et al.

(10) Patent No.: US 9,700,851 B2
(45) Date of Patent: Jul. 11, 2017

(54) PHENOL CROSSLINK FOR SENSOR MEMBRANE

(75) Inventors: Yuan Wang, Mountain Lakes, NJ (US); Raeanne Gifford, Cortland Manor, NY (US)

(73) Assignee: Waveform Technologies, Inc., Salem, NH (US)

( * ) Notice: Subject to any disclaimer, the term of this patent is extended or adjusted under 35 U.S.C. 154(b) by 1122 days.

(21) Appl. No.: 13/107,816

(22) Filed: May 13, 2011

(65) Prior Publication Data
US 2012/0067734 A1 Mar. 22, 2012

Related U.S. Application Data

(60) Provisional application No. 61/334,536, filed on May 13, 2010.

(51) Int. Cl.
*C08G 65/40* (2006.01)
*C25D 11/00* (2006.01)
(Continued)

(52) U.S. Cl.
CPC ......... *B01D 71/72* (2013.01); *B01D 67/0006* (2013.01); *C12Q 1/003* (2013.01); *G01N 27/3274* (2013.01); *A61B 5/14532* (2013.01); *A61B 2562/12* (2013.01); *B01D 2323/30* (2013.01); *G01N 27/40* (2013.01)

(58) Field of Classification Search
USPC .......................................... 205/188; 528/205
See application file for complete search history.

(56) References Cited

U.S. PATENT DOCUMENTS 5,254,223 A   10/1993  Josowicz et al.
6,814,845 B2 * 11/2004  Wilson et al. ............... 204/486
(Continued)

FOREIGN PATENT DOCUMENTS

EP   1790977        5/2007
EP   1790977 A1 *  5/2007
(Continued)

OTHER PUBLICATIONS

Chen et al., "Electrochemically Mediated Electrodeposition/Electropolymerization to yield a Glucose MicroBiosensor with Improved Characteristics", Anal. Chem., 2002, 74 (2) pp. 368-372, Jan. 14, 2002.*
(Continued)

*Primary Examiner* — Mark Kaucher
*Assistant Examiner* — Henry Hu
(74) *Attorney, Agent, or Firm* — Schwabe, Williamson & Wyatt P.C.

(57) ABSTRACT

Embodiments herein provide a membrane that is a product of a phenol crosslinked with one or more compounds containing an allyl group. The phenol may be electropolymerized with the allyl-containing compounds to form the crosslinked polymer. Suitable allyl-containing compounds include allylphenol, allylalcohol, allylamine, and allylcarbamide. A membrane may have one type of allyl-containing compound, or, alternatively, two or more types of compounds. As used in an analyte sensing device, a membrane formed from a crosslinked phenol may provide improved interference exclusion, peroxide response, stability, and/or solvent resistance.

11 Claims, 5 Drawing Sheets

(51) Int. Cl.
  *B01D 71/72*   (2006.01)
  *B01D 67/00*   (2006.01)
  *C12Q 1/00*    (2006.01)
  *G01N 27/327*  (2006.01)
  *A61B 5/145*   (2006.01)
  *G01N 27/40*   (2006.01)

(56) References Cited

U.S. PATENT DOCUMENTS

| | | | |
|---|---|---|---|
| 7,258,769 B2 * | 8/2007 | Cui et al. | 204/403.14 |
| 2003/0000833 A1 * | 1/2003 | Mansouri et al. | 204/402 |
| 2003/0104119 A1 | 6/2003 | Wilson et al. | |
| 2007/0134721 A1 * | 6/2007 | Laitenberger et al. | 435/7.1 |

FOREIGN PATENT DOCUMENTS

| | | |
|---|---|---|
| WO | 94/20602 | 9/1994 |
| WO | WO-2011/143627 A3 * | 11/2011 |

OTHER PUBLICATIONS

Marsh et al., "Poly(2-allyl)phenylene oxide electropolymer film growth on steel", J Applied Polymer Science, 79, 9, pp. 1563-1571, Feb. 28, 2001.*

Hrapovic et al., "Picoamerometric detection of glucose at ultrasmall platinum-based biosensors: Preparation and haracterization", Analytical Chemistry, American Chemical Society, US, vol. 75, No. 14, pp. 3308-3315, Jul. 15, 2003.*

Strein et al., "Charactedzation of submicron-sized carbon electrodes insulated with a phenol-allylphenol copolymer", Analytical Chemistry, American Chemical Society, US, vol. 64, No. 13, pp. 1368-1373, Jul. 1, 1992.*

Hrapovic et al., "Picoamerometric detection of glucose at ultrasmall platinum-based biosensors: Preparation and Characterization", Analytical Chemistry, American Chemical Society, US, vol. 75, No. 14, Jul. 15, 2003.

Stein et al., "Characterization of submicron-sized carbon electrodes insulated with a phenol-allylphenol copolymer", Analytical Chemistry, American Chemical Society, US, vol. 64, No. 13, Jul. 1, 1992.

* cited by examiner

PHENOL CROSSLINK FOR SENSOR MEMBRANE

CROSS REFERENCE TO RELATED APPLICATION

The present application claims priority to U.S. Provisional Patent Application No. 61/334,536, filed May 13, 2010, the entire disclosure of which is hereby incorporated by reference in its entirety.

TECHNICAL FIELD

Embodiments herein relate to sensors and associated membranes, and, more specifically, to a phenol crosslink for a sensor membrane.

BACKGROUND

Continuous glucose monitor (CGM) sensors that utilize hydrogen peroxide ($H_2O_2$) detection may suffer from problems with glucose detection accuracy. The voltage that is needed to oxidize $H_2O_2$ is around 600-700 mV vs Ag/AgCl. At this voltage, some common endogenous and exogenous substances such as ascorbic acid, uric acid, and acetaminophen can be easily oxidized. As a result, a false positive bias is often observed if there is an oxidizing interference substance present.

Research has been conducted to identify an interference barrier that can exclude these oxidizing substances by preventing them from reaching the surface of the electrode where oxidation takes place. A common practice is to apply a polymer film/membrane, which is usually negatively charged, onto the sensor so that the interfering substances (most are negatively charged) will be excluded from the reaction center due to repulsive interaction.

BRIEF DESCRIPTION OF THE DRAWINGS

Embodiments will be readily understood by the following detailed description in conjunction with the accompanying drawings and the appended claims. Embodiments herein are illustrated by way of example and not by way of limitation in the figures of the accompanying drawings.

DETAILED DESCRIPTION OF DISCLOSED EMBODIMENTS

Figure 1:
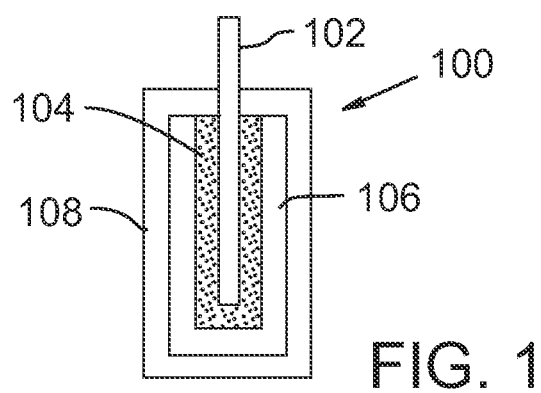
FIG. 1 illustrates an example analyte sensor in accordance with various disclosed embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Various embodiments herein provide a membrane that is a product of a phenol crosslinked with one or more compounds containing an allyl group. The phenol may be electropolymerized with the allyl-containing compounds to form the crosslinked polymer. Suitable allyl-containing compounds include but are not limited to allylphenol, allylalcohol, allylamine, and allylcarbamide. A membrane may have one type of allyl-containing compound, or, alternatively, two or more types of compounds.

As used in an analyte sensing device, for example when used as an interference membrane, a membrane formed from a crosslinked phenol may provide improved interference exclusion, peroxide response, stability, and/or solvent resistance. In addition, it is desirable for such a membrane to have or substantially retain certain flexibility characteristics to permit implantation or semi-implantation in a body without suffering from physical degradation due to normal body movement.

Electro-polymerization of phenol and its derivatives, such as poly(o-phenylenediamine), 1,2-diaminobenzene, and o-aminophenol, have been reported as an interference exclusion barrier. However, such barriers often suffer from declining selectivity during use or in an environment that mimics in-vivo usage.

Phenol electro-polymerization results in generation of polyoxyphenylene, which is only partially solvent resistant. When an outer membrane (OM) that contains solvent, like DMAc, is coated on the sensor, an interference barrier of polyoxyphenylene film is damaged to a certain degree. In accordance with embodiments of the disclosure, with the addition of allyl-containing monomers, such as allylphenol and allylalcohol, the resultant polymer becomes less susceptible to degradation by the organic solvent. As a result, solvent resistance of the membrane is enhanced and use life significantly improves.

The phenol molecule is slightly acidic, and, during polymerization, has tendencies to form a phenoxide anion and further to form a phenoxide radical after loss of one electron. The phenoxide radical undergoes coupling with another phenol molecule. An example polymerization reaction product is shown below:

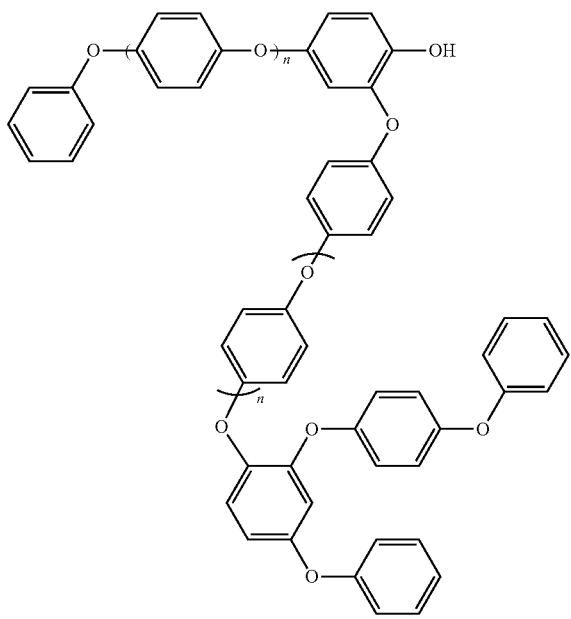

A simplified reaction of 2-allylphenol with phenol is shown below.

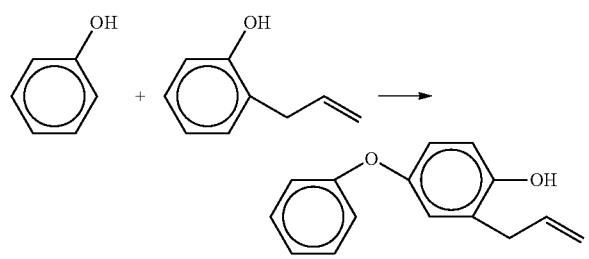

An example reaction product of the polymerization reaction of 2-allylphenol with phenol is shown below.

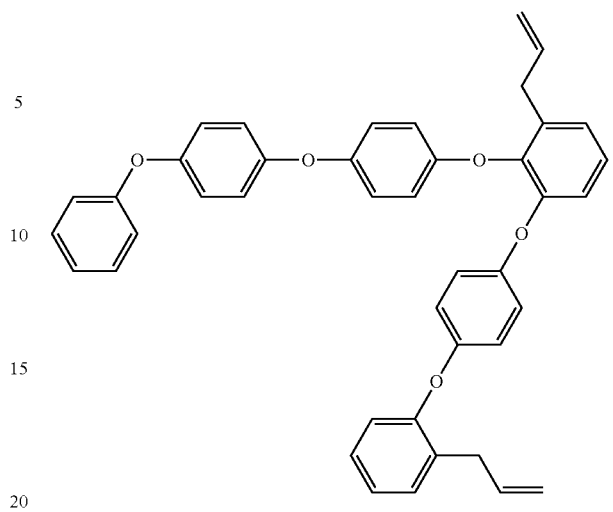

A simplified reaction of 2-allylalcohol with phenol is shown below.

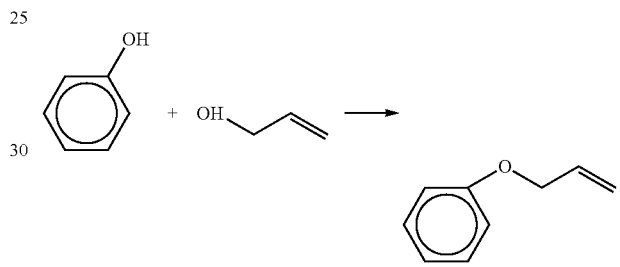

A number of research groups have studied the electro-oxidative polymerization of monomeric phenol derivatives with respect to forming films or coatings on metal substrates. Since such work has generally been conducted for the corrosion protection industry, the experimental conditions are harsher than for a biosensor. A high pH (pH>10) and a solution having a high alcohol content are often used, along with a high voltage. However, in some embodiments herein, the polyphenol layer is immediately deposited on the sensor before or after the enzyme layer. Using a solution that has a high pH and alcohol content may not be suitable and can cause disruption of the enzyme activity. With this limitation in mind, a pH 7.0 PB buffer, or similar solution, may be used for electro-polymerization.

Two example embodiments are described further below: 1) a membrane directly electro-polymerized onto a sensor wire, and 2) a membrane electro-polymerized onto a glucose oxidase coated sensor wire.

1) A Membrane Directly Electro-Polymerized onto a Sensor Wire

Phenol and crosslink monomers (allylphenol, allylalcohol, and allylamine) were electro-polymerized onto a sensor substrate at a polarizing voltage of 0.95V versus Ag/AgCl. A Pt mesh was used as a counter electrode. The resultant films were cured at normal room temperature, at 45° C. overnight, and at 204° C. for 0.5 hour. The selectivity to acetaminophen (APAP) was evaluated and the films' permeability to hydrogen peroxide ($H_2O_2$) was also assessed (see Table 1 below). The average responses of APAP and $H_2O_2$ as well as their standard deviation (SD, n=3) are calculated and listed in Table 1. The ratios of 0.1 mM APAP to 0.1 mM $H_2O_2$ are also calculated and used to evaluate perm-selectivity of the polymer films. The results indicate that polymer films cured at a high temperature (204° C.) had the best APAP to $H_2O_2$ ratio, while acceptable performance was observed for these polymer films cured at normal room condition (20° C.). It seems that polymer films cured at 45° C. do not necessarily have better performance than those cured at 204° C. and normal room temperature (20° C.). The "Ratio" refers to the permeability to APAP compared to that of $H_2O_2$. In accordance with the above, a polymer film may be cured by applying heat at a temperature from 150-250° C.

TABLE 1

| Material | 0.1 mM APAP | SD | 0.1 mM $H_2O_2$ | SD | Ratio | SD |
|---|---|---|---|---|---|---|
| Phenol 20 C. | 5.37 | 1.01 | 63.19 | 28.59 | 9% | 3% |
| Phenol + allylamine 20 C. | 9.31 | 1.00 | 110.87 | 14.15 | 9% | 2% |
| Phenol + allylphenol 20 C. | 87.40 | 3.05 | 1918.73 | 131.39 | 5% | 0% |
| Phenol + allylalcohol 20 C. | 75.23 | 127.19 | 2722.37 | 4558.44 | 2% | 1% |
| Phenol + allylphenol + allylamine 20 C. | 0.13 | 0.06 | 0.83 | 0.32 | 18% | 10% |
| Phenol + allylphenol 45 C. | 76.4 | 11.05 | 1518.63 | 225.52 | 5% | 0% |
| Phenol + allylamine 45 C. | 102.13 | 164.00 | 494.07 | 712.28 | 14% | 8% |
| Phenol + allylalcohol 45 C. | 342.9 | 46.91 | 1386.07 | 254.69 | 25% | 2% |
| Phenol + allylphenol + allylamine 45 C. | 224.73 | 121.58 | 1171.07 | 653.98 | 20% | 2% |
| Phenol + allylamine 204 C. | 148.8 | 77.04 | 3016.43 | 1245.94 | 5% | 1% |
| Phenol + allylphenol 204 C. | 0.63 | 0.26 | 1880.87 | 3191.59 | 1% | 1% |
| Phenol + allylalcohol 204 C. | 341.9 | 139.83 | 4510.3 | 731.52 | 7% | 2% |
| Phenol + allylphenol + allylamine 204 C. | −0.01 | 0.20 | 23.93 | 6.10 | 0% | 1% |

Based on the films' permeability to APAP and hydrogen peroxide, films that exhibited an APAP to hydrogen peroxide ratio less than 15% were selected for solvent compatibility testing. The inner membrane (IM) film layers were applied to the sensor wire. A layer of either electrodeposited glucose oxidase (GOx) or dip coated bovine serum albumin (BSA)/glutaraldehyde was added before a permselective outer membrane (OM) was applied (FIG. 1).

FIG. 1 illustrates an exemplary analyte sensor 100, formed from a sensor 102 having an electrode surface. Various layers/membranes are then formed/deposited on sensor 102, including an inner interference exclusion membrane 104, an enzyme layer 106, and an outer permselective membrane 108.

In various aspects, an analyte sensor herein may be a glucose sensor, an enzyme layer may comprise an enzyme such as glucose oxidase, and/or a permselective membrane may control the relative transmission of glucose and oxygen.

An embodiment provides an analyte sensor comprising an electrically active electrode surface, and a membrane formed from a phenol crosslinked with one or more allyl-containing compounds. The membrane may be disposed on the electrode surface. The term disposed indicates that one membrane or layer is formed or deposited directly on another membrane or layer. An enzyme layer may be further disposed on the membrane. Alternatively, an enzyme layer may be disposed on the electrode surface, and the membrane may be disposed on the enzyme layer. The membrane may be configured to provide interference exclusion, peroxide response, stability, and/or solvent resistance.

In an aspect, the electrically active electrode surface may be formed from a metal, such as tantalum or a noble metal, for example, platinum or palladium.

Figure 2:
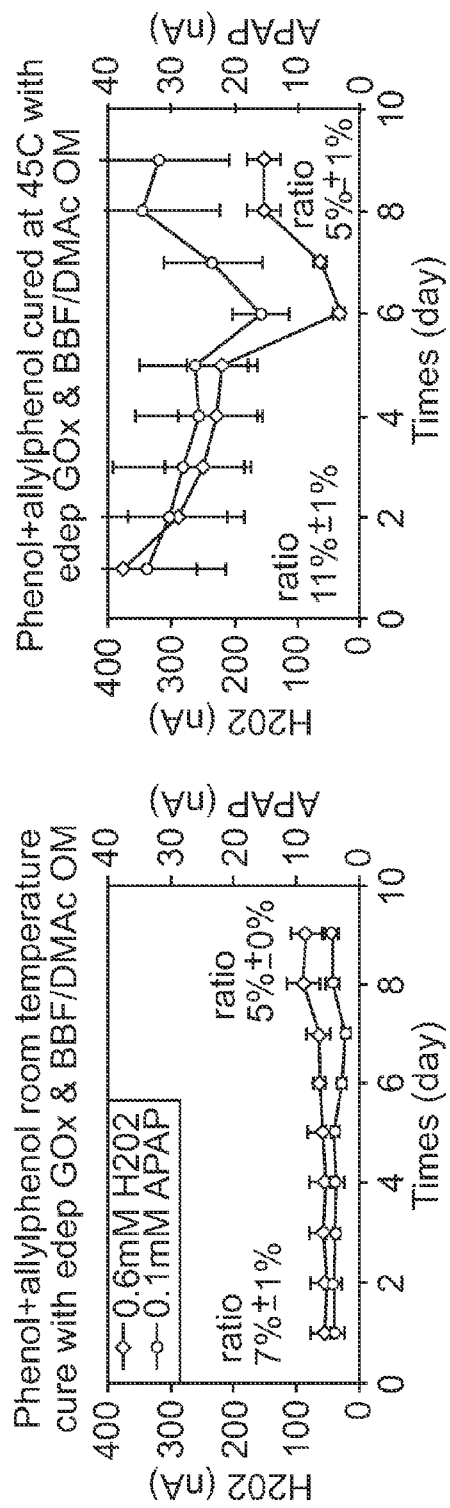
FIGS. 2 and 3 illustrate graphs of use life studies of various analyte sensors in accordance with various embodiments.
Figure 2:
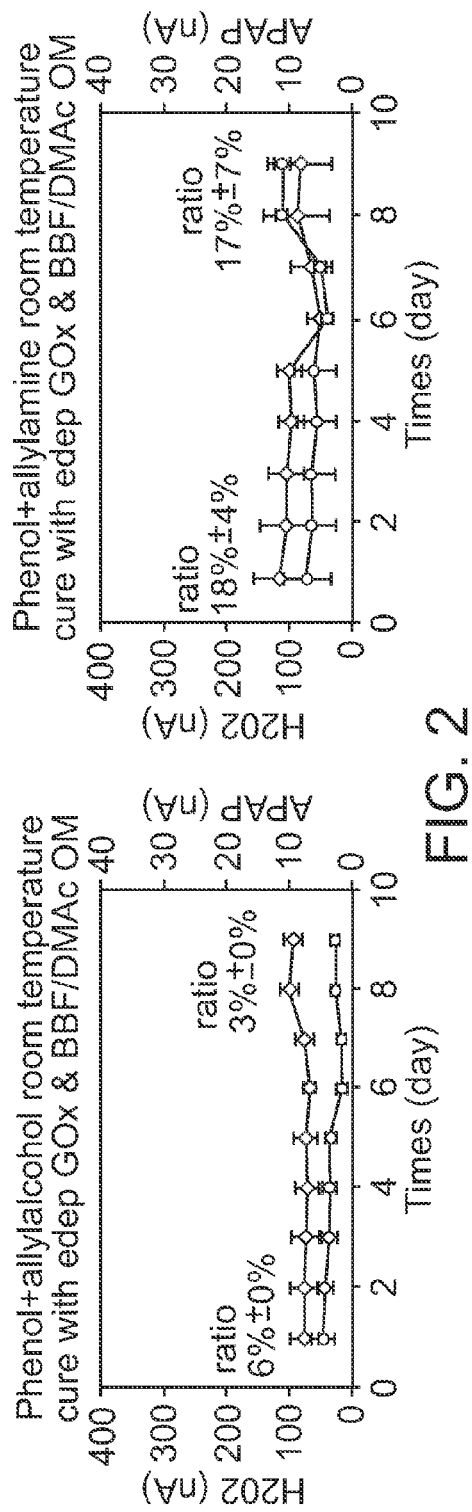
Figure 3:
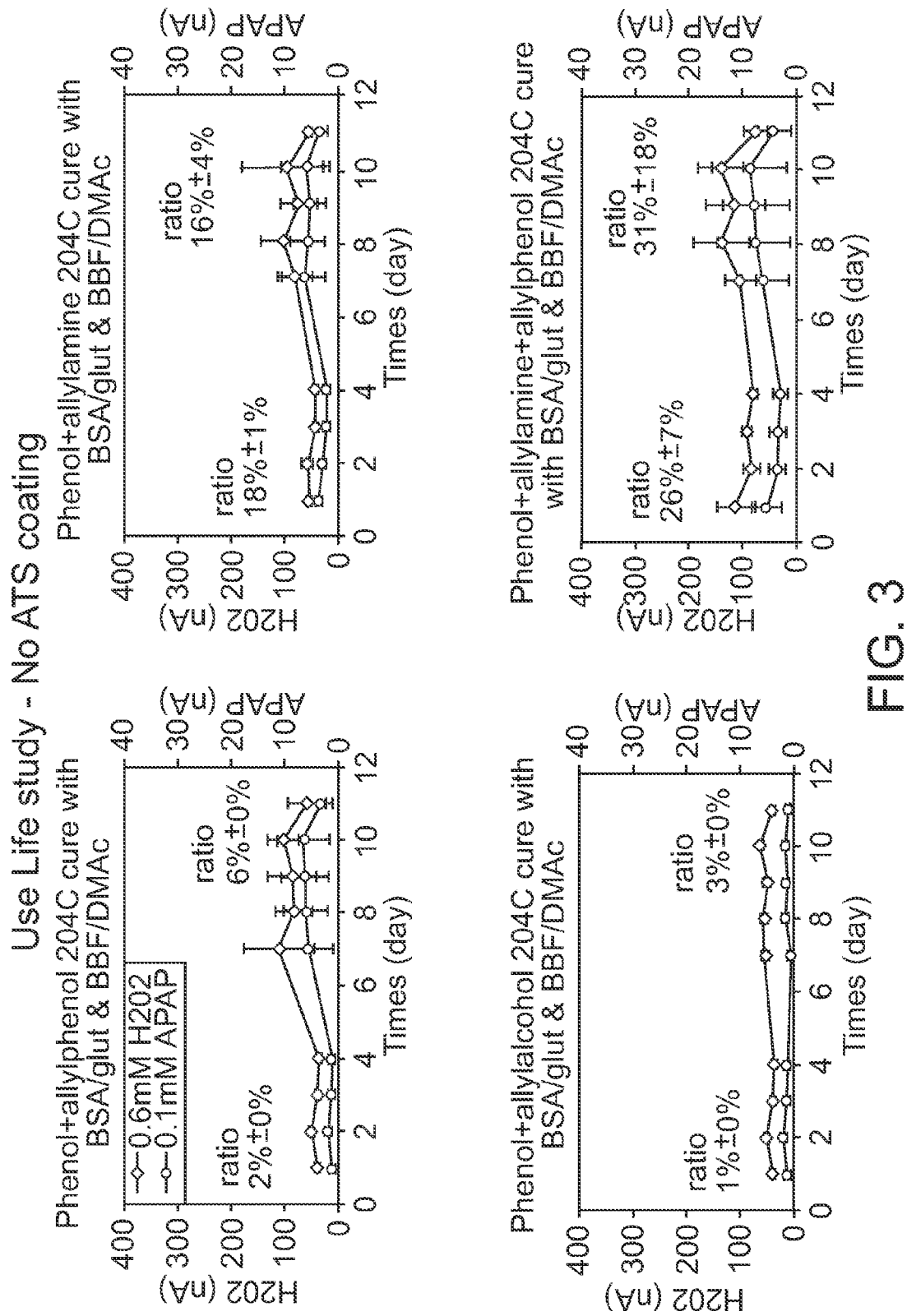

A use life study was conducted in which the sensors were tested with 0.1 mM APAP and 0.6 mM hydrogen peroxide and stored in a solution containing 10 mM glucose and 0.05 mM APAP (37° C.) with continued polarization between the check points for more than 7 days. A very stable response to APAP was observed over the use life testing. Results indicate that the polymers also have excellent resistance to the OM solvent (DMAc), even without a protection layer, whether they are cured at room temperature or 204° C. (FIGS. 2 and 3). The elimination of the protection layer, such as a silane, for example 3-aminopropyltrimethoxysilane (ATS), reduces fabrication time and improves sensor to sensor variation.

2) A Membrane Electro-Polymerized onto a Glucose Oxidase (Enzyme) Coated Sensor Wire Because the polymer films cured at normal room temperature demonstrated good use stability and solvent compatibility, these films were also used to make the CGM sensors utilizing an electro-polymerization method, such as described in U.S. Pat. No. 6,814,845, the contents of which are hereby incorporated by reference.

Figure 4:
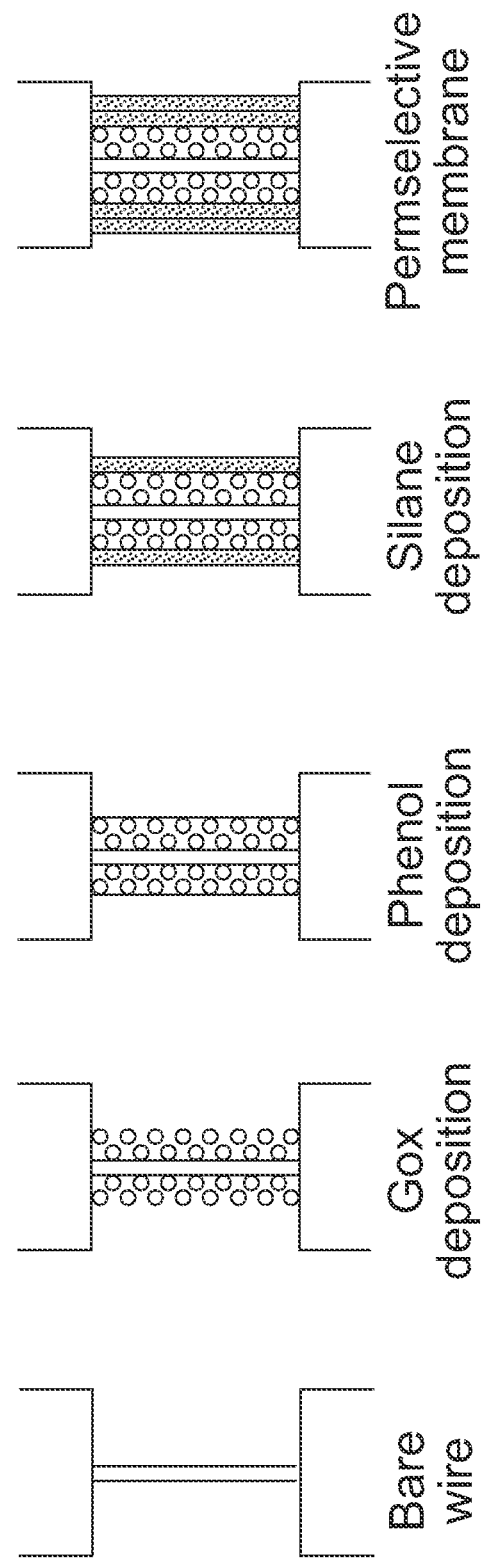
FIG. 4 illustrates an example method for forming an analyte sensor by deposition/application of various membranes/layers in accordance with various embodiments.

FIG. 4 illustrates an example method for forming an analyte sensor by deposition/application of various membranes/layers. Beginning with a bare wire or electrode surface, the membranes/layers are applied sequentially from GOx, to crosslinked phenol, to silane, to a permselective outer membrane.

Figure 5:
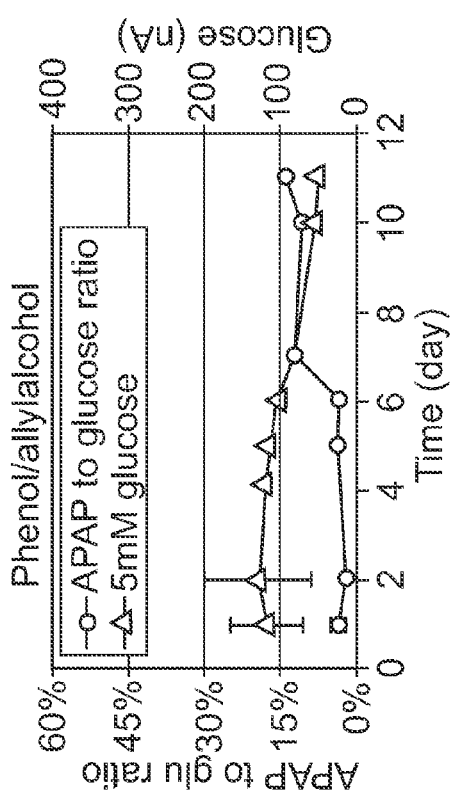
FIG. 5 illustrates graphs of use life studies of various analyte sensors in accordance with various embodiments.
Figure 5:
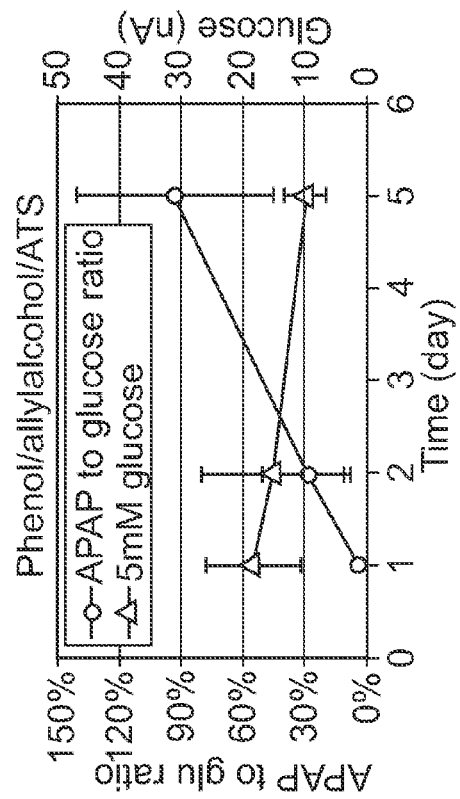
Figure 5:
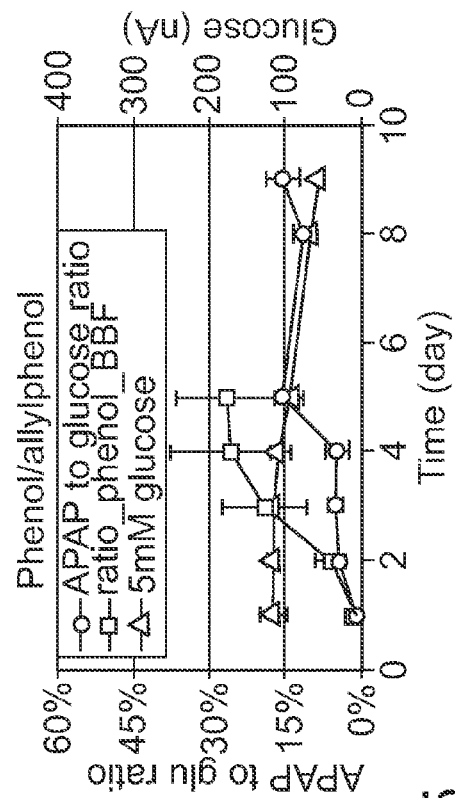
Figure 5:
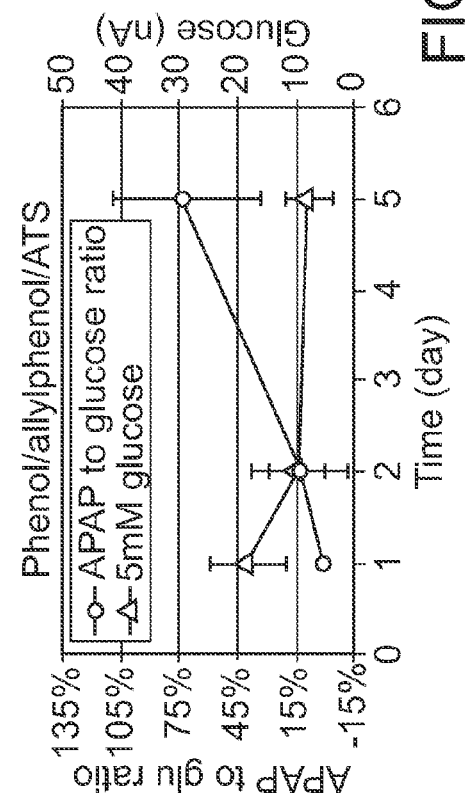

As an example of this method, a GOx/triton X-100 solution is deposited onto a sensor wire first (1.3V vs. Ag/AgCl), followed by phenol (0.9V vs. Ag/AgCl) and ATS (silane) electro-deposition (0.6V vs. Ag/AgCl) (FIG. 4). A bio-compatible, permselective outer membrane was provided as a diffusion barrier to glucose and oxygen. However, the resultant sensors do not maintain a good APAP to glucose ratio if the outer membrane uses an organic solvent. When the polyphenol layer was replaced with crosslinked phenol, the sensor's use life was extended. For sensors with, for example, phenol/allylphenol, the APAP to glucose ratio was maintained at 15% or less for approximately 7 days (FIG. 5). In addition, it was determined that the sensors have good solvent compatibility and there is no need to have a protective ATS coating. And, electro-deposition provides a more controllable manufacturing process in comparison to multi-dipping processes.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An interference exclusion membrane, consisting essentially of phenol crosslinked by one or more of allylalcohol, allylamine, and allylcarbamide.

2. The membrane of claim 1, wherein the phenol is crosslinked by one of allylalcohol, allylamine, and allylcarbamide.

3. The membrane of claim 2, consisting essentially of phenol crosslinked by allylalcohol.

4. The membrane of claim 2, consisting essentially of phenol crosslinked by allylamine.

5. The membrane of claim 2, consisting essentially of phenol crosslinked by allylcarbamide.

6. The membrane of claim 1, wherein the phenol is crosslinked by two of allylalcohol, allylamine, and allylcarbamide.

7. An analyte sensor, comprising:
the interference exclusion membrane of claim 1; and
an electrically active electrode surface.

8. The analyte sensor of claim 7, wherein the interference exclusion membrane is disposed on the electrically active electrode surface.

9. The analyte sensor of claim 8, further comprising an enzyme layer disposed on the interference exclusion membrane.

10. The analyte sensor of claim 7, further comprising an enzyme layer disposed on the electrically active electrode surface, wherein the interference exclusion membrane is disposed on the enzyme layer.

11. The analyte sensor of claim 7, wherein the interference exclusion membrane is configured to provide interference exclusion, peroxide response, stability, and/or solvent resistance.

* * * * *